(12) United States Patent
Davies et al.

(10) Patent No.: US 11,357,953 B2
(45) Date of Patent: Jun. 14, 2022

(54) FEEDBACK MECHANISMS FOR A STEERABLE MEDICAL DEVICE

(71) Applicant: Baylis Medical Company Inc., Montreal (CA)

(72) Inventors: Gareth Davies, Toronto (CA); Melanie Thompson Smith, Toronto (CA); Jan-Hung Chen, Georgetown (CA); Ahmed Alnabelseya, Ottawa (CA); Audrey Chan, Richmond Hill (CA); Andrew Pequegnat, Cambridge (CA); Moussa Chehade, Toronto (CA)

(73) Assignee: Baylis Medical Company Inc., Mississauga (CA)

( * ) Notice: Subject to any disclaimer, the term of this patent is extended or adjusted under 35 U.S.C. 154(b) by 385 days.

(21) Appl. No.: 15/851,942

(22) Filed: Dec. 22, 2017

(65) Prior Publication Data

US 2018/0214669 A1      Aug. 2, 2018

Related U.S. Application Data

(60) Provisional application No. 62/437,916, filed on Dec. 22, 2016.

(51) Int. Cl.
*A61M 25/01* (2006.01)
*A61B 90/00* (2016.01)

(52) U.S. Cl.
CPC .... *A61M 25/0136* (2013.01); *A61M 25/0147* (2013.01); *A61B 2090/0811* (2016.02); *A61M 2205/581* (2013.01); *A61M 2205/582* (2013.01); *A61M 2205/583* (2013.01)

(58) Field of Classification Search
CPC .......... A61M 25/0136; A61M 25/0147; A61M 2205/581; A61M 2205/582; A61M 2205/583; A61M 25/0133; A61N 2090/0811
See application file for complete search history.

(56) References Cited

U.S. PATENT DOCUMENTS

| | | | |
|---|---|---|---|
| 4,294,233 A | 10/1981 | Takahashi | |
| 5,228,441 A * | 7/1993 | Lundquist | A61B 18/1492 600/380 |
| 5,364,351 A | 11/1994 | Heinzelman et al. | |
| 5,395,327 A | 3/1995 | Lundquist et al. | |

(Continued)

FOREIGN PATENT DOCUMENTS

| | | |
|---|---|---|
| EP | 0904797 | 3/1999 |
| EP | 3985423 A2 | 3/2000 |

(Continued)

*Primary Examiner* — Lauren P Farrar
*Assistant Examiner* — Hamza A Darb
(74) *Attorney, Agent, or Firm* — Samuel Tekie; Glenn Arnold; Vincent Man

(57) ABSTRACT

An apparatus and method are disclosed for providing feedback for a steerable medical device assembly for deflecting a device, the assembly comprising a control handle comprising an actuation mechanism. The assembly additionally comprises a device coupled to the control handle and operable to be deflected upon actuation of the actuation mechanism, and a feedback mechanism for providing an indication of the deflection of the device, wherein the feedback mechanism is associated with the actuation mechanism for deflecting the device.

18 Claims, 12 Drawing Sheets

(56) References Cited

U.S. PATENT DOCUMENTS

| | | |
|---|---|---|
| 5,395,329 A | 3/1995 | Fleischhacker |
| 5,462,527 A | 10/1995 | Stevens-Wright |
| 5,571,085 A | 11/1996 | Accisano, III |
| 5,626,136 A | 5/1997 | Webster, Jr. |
| 5,779,669 A | 7/1998 | Haissaguerre et al. |
| 5,891,088 A | 4/1999 | Thompson |
| 5,938,616 A | 8/1999 | Eaton |
| 5,944,690 A | 8/1999 | Fallwell et al. |
| 6,059,739 A | 5/2000 | Baumann |
| 6,245,045 B1 | 6/2001 | Stratienko |
| 6,551,302 B1 | 4/2003 | Rosinko et al. |
| 7,497,853 B2 | 3/2009 | Fischer et al. |
| 7,524,301 B2 | 4/2009 | Dubois et al. |
| 7,615,044 B2 | 11/2009 | Scheibe et al. |
| 7,637,932 B2 | 12/2009 | Bolduc et al. |
| 7,691,095 B2 | 4/2010 | Bednarek et al. |
| 7,959,601 B2 | 6/2011 | McDaniel et al. |
| 8,056,207 B2 | 11/2011 | Honebrink et al. |
| 8,123,721 B2 | 2/2012 | Tegg |
| 8,308,659 B2 | 11/2012 | Scheibe et al. |
| 8,460,237 B2 | 6/2013 | Schultz |
| 8,676,290 B2 | 3/2014 | Tegg |
| 8,845,717 B2 | 9/2014 | Khairkhahan et al. |
| 8,858,495 B2 | 10/2014 | Tegg et al. |
| 8,911,397 B2 | 12/2014 | O'Donnell et al. |
| 9,149,607 B2 | 10/2015 | Scheibe et al. |
| 9,149,608 B2 | 10/2015 | O'Donnell et al. |
| 2003/0109861 A1 | 6/2003 | Shimada |
| 2006/0142699 A1 | 6/2006 | Lampropoulos |
| 2006/0184106 A1 | 8/2006 | McDaniel et al. |
| 2007/0260223 A1 | 11/2007 | Scheibe et al. |
| 2009/0281524 A1 | 11/2009 | Scheibe et al. |
| 2010/0004592 A1 | 1/2010 | Butler |
| 2010/0069834 A1 | 3/2010 | Schultz |
| 2010/0164137 A1 | 7/2010 | Selkee |
| 2011/0054287 A1 | 3/2011 | Schultz |
| 2011/0054446 A1 | 3/2011 | Schultz |
| 2011/0282176 A1 | 11/2011 | Tegg |
| 2012/0089125 A1 | 4/2012 | Scheibe et al. |
| 2012/0109079 A1 | 5/2012 | Asleson et al. |
| 2012/0203169 A1 | 8/2012 | Tegg |
| 2013/0030520 A1 | 1/2013 | Lee |
| 2013/0102960 A1 | 4/2013 | Miyoshi |
| 2013/0165857 A1 | 6/2013 | O'Donnell et al. |
| 2013/0184642 A1* | 7/2013 | O'Donnell ........ A61M 25/0102 604/95.04 |
| 2014/0018732 A1 | 1/2014 | Bagaoisan et al. |
| 2014/0088496 A1 | 3/2014 | Tegg |
| 2015/0231366 A1* | 8/2015 | Davies .............. A61M 25/0136 604/95.04 |

FOREIGN PATENT DOCUMENTS

| | | |
|---|---|---|
| EP | 1050316 | 11/2000 |
| EP | 1323448 | 7/2003 |
| EP | 1607118 | 12/2005 |
| EP | 1676595 | 7/2006 |
| EP | 1676595 A1 | 7/2006 |
| EP | 1897581 | 3/2008 |
| EP | 2018203 | 1/2009 |
| EP | 2116272 | 11/2009 |
| EP | 2204208 | 7/2010 |
| EP | 2289408 A1 | 3/2011 |
| EP | 2438954 | 4/2012 |
| EP | 2465568 | 6/2012 |
| JP | H02-289223 | 11/1990 |
| JP | 2001516257 | 9/2001 |
| JP | 2004-532074 | 10/2004 |
| JP | 2006-187606 | 7/2006 |
| JP | 2006187606 | 7/2006 |
| JP | 2010-194102 | 9/2010 |
| JP | 2010194102 | 9/2010 |
| WO | 1995005116 | 2/1995 |
| WO | 199637252 | 11/1996 |
| WO | 199841275 | 9/1998 |
| WO | 2000067834 | 11/2000 |
| WO | 2007136984 | 11/2007 |
| WO | 2013016681 A2 | 1/2013 |
| WO | 2013096676 | 6/2013 |
| WO | 2013096694 | 6/2013 |
| WO | 2013190475 A2 | 12/2013 |
| WO | WO-2013190475 A2 * | 12/2013 ........ A61M 25/0136 |
| WO | 2012132636 | 7/2014 |

\* cited by examiner

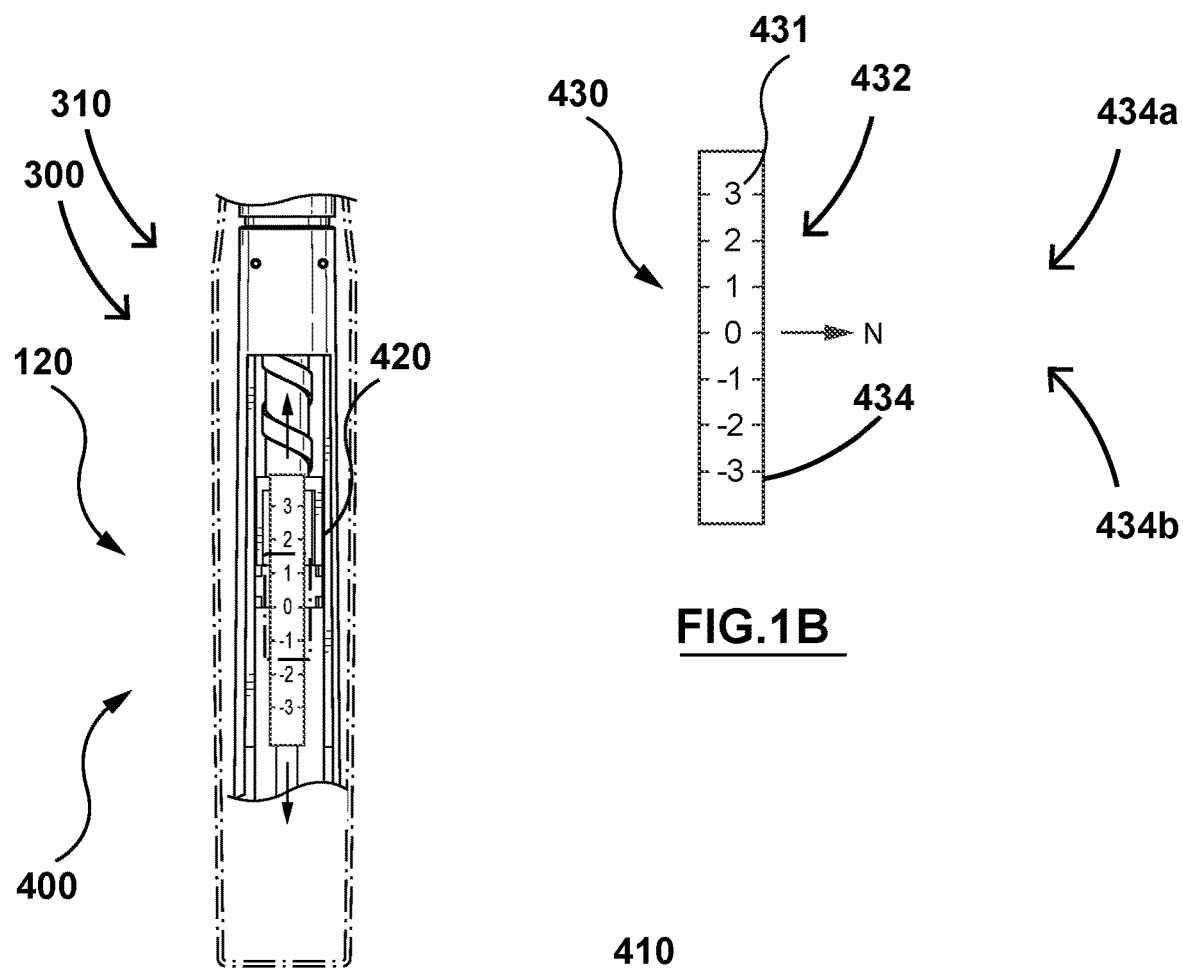
FIG.1B
FIG.1A
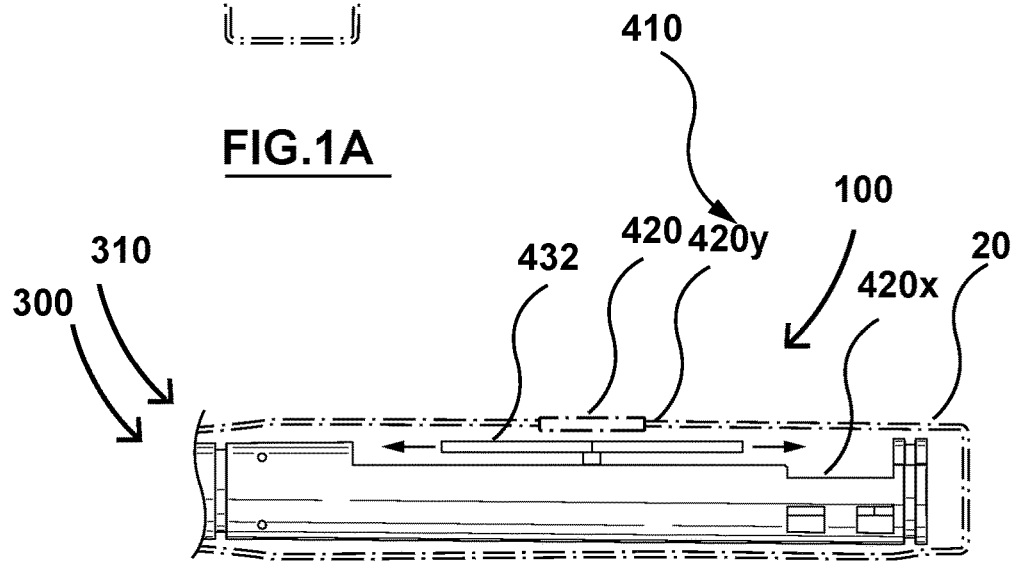
FIG.1C

FEEDBACK MECHANISMS FOR A STEERABLE MEDICAL DEVICE

TECHNICAL FIELD

The disclosure relates to a steerable sheath handle. More specifically, the present disclosure relates to a mechanism for providing neutral zone feedback for a steerable sheath handle.

BRIEF DESCRIPTION OF THE DRAWINGS

In order that the invention may be readily understood, embodiments of the invention are illustrated by way of examples in the accompanying drawings, in which:

FIGS. 1A-1C are an illustration of a feedback mechanism comprising a visual feedback mechanism for steerable catheter assembly, in accordance with an embodiment of the present invention;

DETAILED DESCRIPTION

Figure 2A:
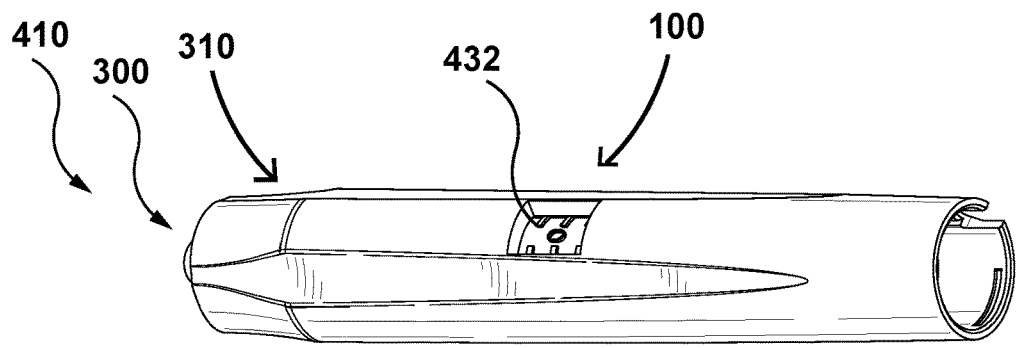
FIGS. 2A-2D are an illustration of a feedback mechanism comprising a visual feedback mechanism for a steerable catheter assembly, in accordance with an embodiment of the present invention.
Figure 2B:
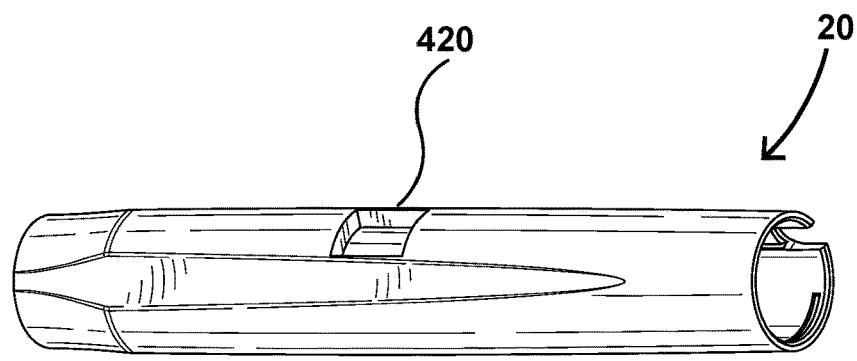
Figure 2C:
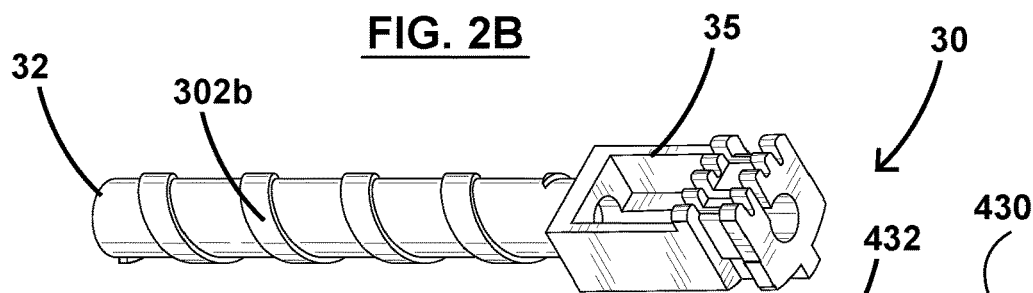
Figure 2D:
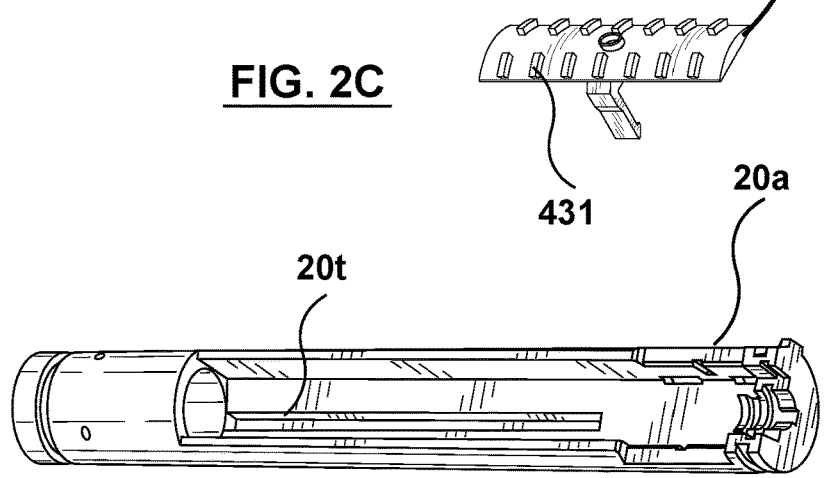

In certain medical interventional procedures a steerable medical device such as a steerable sheath assembly or system may be utilized by physicians to gain access to a target location within the body. A control system or mechanism may be operable to deflect a sheath or catheter. However, it may be difficult for some physicians when operating such a steerable control mechanism of the steerable to ascertain how the sheath curving. It may be hard for the user to determine how the sheath or catheter is behaving in response to the operation of the control system, for example in instances where the sheath or catheter is not visible to the user. For example, when in use within a patient's body, the physician's view is obstructed once the sheath or catheter is positioned inside the patient's body.

As such, it may be difficult to determine the behavior of the curving or deflecting portion of the sheath, for example when a visual reference or context is not available, upon actuation of the control mechanism. The user may not be able to determine how much the sheath is curving or in other words, the user may not be able to determine the level or degree of deflection of the sheath or catheter. In other words, it may be difficult to ascertain from the portion of the steerable sheath assembly that is visible or accessible to the user, [i.e. the steerable catheter control handle, such as a portion of the actuation mechanism thereof, such as an actuator such a knob], the behavior of the component of the assembly that is not visible or removed from the user [such as the sheath or catheter]. As such, the portion of the steerable sheath assembly that is visible to the user, such as the actuator (or the position thereof) may not provide adequate information on the behavior (or position such as deflection position) of the portion of the steerable sheath assembly, the sheath that is not visible to, or accessible to the user.

As such, as an example of this, it may be difficult for the physician to ascertain when they are in the neutral zone, or how far away they are from it—the neutral zone being the region where neither of the deflection wires is placed under tension. Thus, there is a need in the art to provide a steerable control system for a steerable sheath that provides neutral zone feedback.

The present inventors have discovered a novel apparatus and method for a steerable catheter (control) system or assembly (comprising a control handle that is coupled to a sheath and operable to deflect the same) that provides a feedback mechanism to provide an indication for the behavior of the portion of the steerable sheath assembly, the sheath that is not visible to, or removed from the user. In some such embodiments, the feedback mechanism is provided on or associated with a portion of the steerable sheath assembly that is visible or accessible to the user, such as the steerable control handle that provides an indication of the sheath that is not visible to, or removed from the user. In some such embodiments, the feedback mechanism is provided on or associated with an actuation mechanism of the steerable control handle. In some such embodiments the feedback mechanism provides an indication of the deflection of the sheath or catheter, such as how much the sheath or catheter is being deflected. In other words, a feedback mechanism is provided that provides an indication of the state (or position) of the sheath or catheter, such as the state of deflection (or deflection position) of the sheath or catheter in response to an actuation of the actuation mechanism (or in other words that corresponds to an actuation state or position of the actuation mechanism and/or an actuator of the actuation mechanism). In some such embodiments, the feedback mechanism provides an indication to the user of whether the sheath or catheter is in its deflected state or un-deflected state that is indicative of a neutral position of neutral zone of the control handle and the sheath or catheter. In some embodiments, the feedback mechanism additionally provides feedback of the level or degree of deflection of the sheath or catheter, for example in the deflected state upon actuation of the control handle or system.

The feedback mechanism may be particularly useful where the sheath or catheter is deflected and the view of the sheath or catheter, such as that of the deflecting portion of the sheath or catheter, may be obstructed or may not be readily visible, such as when the sheath or catheter is used inside the patient's body. In some such examples the feedback mechanism provides an indication mechanism when the catheter control mechanism or assembly and as such the deflectable distal end of the sheath is in its neutral position. More specifically in accordance with an embodiment of the present invention, a mechanism is provided for identifying the deflection of the sheath or catheter, and in some such examples a mechanism is provided for identifying neutral zone. In some such embodiments a feedback mechanism is provided that provides an indication through sensory feedback. In one such example the feedback mechanism provides an indication through tactile feedback. In other examples an indication is provided through visual feedback. In still other examples an indication is provided through audible feedback.

In accordance with some embodiments of the present invention a steerable catheter control handle assembly is provided for deflecting a catheter that comprises a control knob that is operational to deflect the distal end of the sheath or catheter by causing linear movement of a slide assembly within a track of the inner housing of the handle, to actuate one of the two pull wires of the sheath to deflect a distal end of the sheath. In some such embodiments, a feedback mechanism is provided within the steerable catheter control handle for providing an indication of the deflection of the sheath or catheter, wherein the feedback mechanism is associated with the control mechanism or system provided within the steerable catheter control handle for deflecting the device.

In accordance with some such embodiments of the present invention a method and apparatus are disclosed for a steerable catheter control handle assembly that comprises a steerable catheter control handle that provides feedback to assist the physician in identifying the deflection of the sheath or catheter. In some such examples, a steerable catheter control handle is provided that provides feedback to assist the physician in identifying the neutral zone. In some such embodiments, the feedback is in the form of an indicator.

In one broad aspect, embodiments of the present invention provide a steerable medical device assembly (such as a steerable catheter control handle assembly) for deflecting a device (such as sheath or catheter) and/or to provide feedback, the steerable medical device assembly (such as the steerable catheter control handle assembly) comprising a control handle comprising an actuation mechanism for deflecting the device (such as the sheath or catheter), the device (such as the sheath or catheter) being coupled to the control handle and operable to be deflected upon actuation of the actuation mechanism, and a feedback mechanism for providing an indication of the deflection of the device (such as the sheath or catheter), wherein the feedback mechanism is associated with the actuation mechanism for deflecting the device (such as the sheath or catheter).

In one broad aspect embodiments of the present invention comprises a steerable medical device assembly for deflecting a device comprising a control handle comprising an actuation mechanism, a device coupled to the control handle and operable to be deflected upon actuation of the actuation mechanism; and a feedback mechanism for providing an indication of the deflection of the device; wherein the feedback mechanism associated with the actuation mechanism for deflecting the device.

As a feature of this broad aspect, the feedback mechanism provides sensory feedback.

As a feature of this broad aspect, the feedback mechanism comprises a visual feedback mechanism that provides a visual indication. As an example of this feature, the visual feedback mechanism comprises a mechanical feedback mechanism.

In a specific example of this, the mechanical feedback mechanism comprises a window that is formed within a housing of the control handle; and one or more alignment markings associated with the actuation mechanism for deflecting the catheter, and wherein the visibility of the one or more alignment markings through the window corresponds to and is indicative of a deflection position of the device (such as a catheter) and a corresponding position of the actuation mechanism to provide a visual indication of the deflection position of the device (such as the catheter) upon actuation of the actuation mechanism. In another specific example, the mechanical feedback mechanism comprises: one or more alignment markings associated with the actuation mechanism for deflecting the device (such as the catheter); and one or more indicator markings that are associated with a housing of the control handle; wherein the relative arrangement of the one or more alignment markings and the one or more indicator markings corresponds to and is indicative of a deflection position of the device (such as the catheter) and a corresponding position of the actuation mechanism to provide a visual indication of the deflection position of the catheter upon actuation of the actuation mechanism.

As another example of this feature, the visual feedback mechanism comprises an electrical feedback mechanism. In a specific example of this, the electrical feedback mechanism comprises: a light emitting source or device, wherein the light emitting source has an active state where the light emitting source or device is operable to emit light and a passive state where the light emitting source is off; and a sensor coupled to the light emitting source or device for detecting a position of a portion of the actuation mechanism; wherein the light emitting device is operable to be in its active state upon detection of the position of the portion of the actuation mechanism by the sensor, and corresponds to and is indicative of a deflection position of the device (such as the catheter) and a corresponding position of the actuation mechanism to provide a visual indication of the deflection position of the device (such as the catheter) upon actuation of the actuation mechanism. In one instance of this example, the light emitting source comprises an LED.

As still another feature of this broad aspect, the feedback mechanism provides comprises a tactile feedback mechanism that provides a tactile indication.

As an example of this feature, the tactile feedback mechanism comprises a mechanical feedback mechanism. In a specific of this, the mechanical feedback mechanism comprises a first indicator portion associate with a housing of the control handle, and a second indicator portion associated with the actuation mechanism for deflecting the device (such as the catheter), wherein the interaction between the first and second indicator portions corresponds to and is indicative of a deflection position of the device (such as the catheter) and a corresponding position of the actuation mechanism to provide a tactile indication of the deflection position of the device (such as the catheter) upon actuation of the actuation mechanism.

As still another feature of this broad aspect, the feedback mechanism comprises an audible feedback mechanism that provides an audible indication.

As an example of this feature, the audible feedback mechanism comprises a mechanical feedback mechanism.

In a specific example of this feature, the mechanical feedback mechanism comprises a first indicator portion associate with a housing of the control handle, and a second indicator portion associated with the actuation mechanism for deflecting the device (such as the catheter), wherein the interaction between the first and second indicator portions corresponds to and is indicative of a deflection position of the device (such as the catheter) and a corresponding position of the actuation mechanism to provide an audible indication of the deflection position of the device (such as the catheter) upon actuation of the actuation mechanism.

As another example of this feature, the audible feedback mechanism comprises an electrical feedback mechanism. In a specific example of this, the electrical feedback mechanism comprises a sound emitting device, the sound emitting device has an active state where the sound emitting device is operable to emit a sound and a passive state where the sound emitting device is off, a sensor coupled to the sound emitting device for detecting a position of (a portion of) the actuation mechanism (such as a slide assembly), wherein the light emitting source is operable to be in its active state upon detection of the position of the actuation mechanism by the sensor, wherein the active state corresponds to and is indicative of a deflection position of the device (such as the catheter) and a corresponding position of the actuation mechanism to provide an audible indication of the deflection position of the device (such as the catheter) upon actuation of the actuation mechanism. In a specific instance of this example, the sound emitting device comprises a buzzer.

In some embodiments, the feedback mechanism provides an indication of degree of deflection of the device (such as the catheter) upon actuation of the actuation mechanism.

In some embodiments, the feedback mechanism provides an indication of neutral zone of the control handle and the device (such as the catheter). In other words, the feedback mechanism provides an indication of a neutral zone of the control handle and the device (such as the catheter) upon the control handle and the device (such as the catheter) being in the neutral zone.

In one such example, the feedback mechanism provides an indication upon actuation mechanism and the device (such as the catheter) exiting the neutral zone.

In some embodiments of the steerable medical device for providing feedback, the actuation mechanism comprises an actuator comprising a control knob, and a slide assembly that is coupled to the control knob via a threadable arrangement, the slide assembly being operable to coupled to the catheter, wherein actuation of the control knob via rotational movement thereof results in linear movement of the slide assembly to deflect the catheter.

In some embodiments, the feedback mechanism provides an indication of the deflection of the device in absence of visual feedback of the deflection of the device.

In some embodiments, the feedback mechanism comprises a mechanical feedback mechanism.

In some embodiments, the feedback mechanism comprises an electrical feedback mechanism.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

In some embodiments of the present invention a feedback mechanism is provided for a steerable medical device assembly comprising a control handle. The control handle comprises an actuation mechanism for deflecting the device. A device is coupled to the control handle and operable to be deflected upon actuation of the actuation mechanism. The steerable medical device assembly (such as a control handle thereof) additionally comprises a feedback mechanism for providing an indication of the deflection of the device, wherein the feedback mechanism is associated with the actuation mechanism for deflecting the sheath or catheter.

In some embodiments of the present invention, with reference now to FIGS. 1A, 1B, 1C, and FIGS. 2A, 2B, 2C, 2D a feedback mechanism 300 is provided for a steerable catheter control system or assembly comprising a steerable catheter control handle 100. A device comprising a sheath or catheter is coupled to the steerable catheter control handle 100 and operable to be deflected upon actuation of an actuation mechanism 200. In one example the control handle 100 is coupled to a proximal end of the sheath or catheter to effect deflection of the distal end of the sheath or catheter. The steerable catheter control handle 100 comprises the actuation mechanism 200 for deflecting the sheath or catheter.

The actuation mechanism 200 in some examples comprises a rotation to linear translation system 220. In one such example, the actuation mechanism 200 comprises a rotatable knob 10 and a slide assembly 30 that it is configured to threadably engage with (for example via a threadable engagement between external threads 302 of the bolt 32 of the slide assembly 30 and corresponding internal threads of the knob 10), where the knob 10 is turned to linearly move the slide assembly 30 within the housing 20 (for example an internal or inner housing 20a, or specifically along a track 20t of the inner housing 20a) that is configured to actuate the catheter coupled thereto. In some examples, one or more pull wires or control wires are provided in the actuation mechanism 200 that have a proximal end that is coupled to the slide assembly and a distal end that is coupled to the catheter (for example at a distal end thereof), where movement of the slide assembly 30 upon actuation of the knob 10, results in deflection of the pull wires, resulting in deflection of the catheter.

The steerable catheter control assembly (specifically the steerable catheter control handle 100 thereof) additionally comprises a feedback mechanism 300 for providing an indication of the deflection of the sheath or catheter, wherein the feedback mechanism 300 is associated with the actuation mechanism 200 for deflecting the sheath or catheter. As such, in some examples the control handle 100 provides a feedback mechanism 300 for providing feedback to assist the physician in identifying or determining the deflection of the sheath or catheter. In some examples, the feedback mechanism 300 provides neutral zone feedback to assist the physician in identifying or determining the neutral zone [N] where the sheath or catheter is substantially un-deflected.

With reference again to FIGS. 1A-1C, wherein the feedback mechanism 300 provides sensory feedback. In the present example, the feedback mechanism 300 comprises a visual feedback mechanism 310 that provides a visual indication. In some such embodiments, as shown in FIGS. 1A, 1B and 1C, and additionally in FIGS. 2A, 2B, 2C, and 2D, the visual feedback mechanism 310 comprises a mechanical feedback mechanism 410. In the specific example shown, the mechanical feedback mechanism 410 comprises a window 420 that is formed within a housing 20 of the control handle 100. In some such examples, the window 420 (as shown in FIGS. 1A, 1C and functions as a first indicator portion. The control handle 100 additionally comprises graduations or markings 430 such as one or more alignment markings 431 that are associated with or provided on (one or more portions of) the actuation mechanism 200 (such as a rotation to linear actuation or translation mechanism 220, as described hereinabove) for deflecting the catheter. In some such examples, the graduations or markings 430 function as a second indicator portion. In a particular example as shown in FIGS. 1A, 1C, and FIGS. 2A, 2B), the graduations or markings 430 such as the one or more alignment markings 431 are provided on a cover or cap or an additional component 432 of the slide assembly 30, that is operable to be coupled to the slide assembly 30 (particularly the slide 35 of the slide assembly 30). The graduations or markings 430 such as the one or more alignment markings 431 thus move with the movement of the slide assembly 30 upon actuation of the knob 10.

The visibility of the graduations or markings 430 such as one or more alignment markings 431 through the window 420 (as shown in FIG. 1A, 2A) corresponds to and is indicative of a deflection position of the catheter and in some examples is additionally indicative of a corresponding position of the actuation mechanism 200 (such as the rotation of linear translation or actuation mechanism 220) to provide a visual indication of the deflection position of the catheter 90 upon actuation of the actuation mechanism 200. The location and or length of the window 420 along the housing 20 of the handle 100 may be varied in order to provide an indication of the degree of deflection of the catheter and/or the location of the neutral zone.

In one such embodiment of a feedback mechanism 300 comprising a visual feedback mechanism 310, with reference again to FIGS. 1A-1C, comprising a mechanical feedback mechanism 410, the present inventors have developed an improved steerable handle that incorporates a steerable sheath handle assembly. The steerable sheath handle assembly comprises a sheath or catheter coupled to a steerable sheath handle [an embodiment of the disclosure provided in in U.S. provisional patent application Ser. No. 61/661,664, in PCT application serial number PCT/IB2013/055013 and in PCT application serial number PCT/IB2017/058137, which have been incorporated herein by reference, in their entirety]. In some such examples, the improved steerable sheath handle provides enhanced quality and increased precision in providing handle position feedback to users.

An embodiment of the present invention provides a mechanical feedback mechanism comprising one or more graduations or markings 430 comprising one or more alignment markings 430 provided on an additional component 432 of the actuation mechanism such as a slide assembly 30. In one such example with reference to FIGS. 1A-1C, the additional component 432 comprises a position indicator strip 434 that is connected for example to the slider 35 of the slide assembly 30 in the control handle 100. In one such example, the indicator strip 434 has two indicator halves (first half 434a, second half 434b) of different colors, separated by a line indicating the neutral position [N] of the slide assembly 30 (such as slider 35 of the slide assembly 30) (i.e. the neutral line [N]; see FIG. 1B). The window 420 as described previously, in the present example, is provided on the handle housing 20 (for example an outer handle casing of the handle housing 20) that allows the user the view a portion of the position indicator strip 434. In one such example as shown, the visibility of the indicator strip 434 through the window 420 indicates if the handle position is neutral [N], as both halves 434a, 434b are visible through the window 420 [for example the different colors with the neutral line in the middle are visible]. As the knob 10 is turned to move the slide assembly 30 (and as such slider 35) up or down, the position indicator or indicator strip 434 moves up or down with the slider 35 and therefore shows a different portion/and/or color of the indicator strip 434 through the window 420 allowing the user to view a portion of the position indicator strip 434. If the handle position is neutral, the user would see through the window 420 both halves 434a, 434b and as such both colors with the neutral line [N] in the middle. As the user turns the knob 10 to move the slider 35 up or down, the position indicator 434 moves up or down with the slider 35 and therefore shows a different portion and/or color [and thus a different portion of the halves 434a, 434b] of the indicator strip 434 through the window 420.

For example, as shown in FIGS. 1A-1C, in one such example if the slider 35 moves up, the user would only see the first half 434a at one point (which for example comprises a blue color) through the window 420. As such, in some examples, the color and the neutral line [N] of the indicator strip 434 then serve to inform the user the position of the actuation mechanism (and as such the actuator such as a knob 10) or in other words the handle position of the steerable control handle 100 of the steerable catheter assembly. Alternatively, instead of using colors, lines and numbers could be used to on the indicator strip 434 to mark the relative handle position with respect to the curvature or deflection of the sheath or catheter and/or the neutral position. In some such embodiments, the indicator strip 434 shows the user where the neutral zone [N] is, and also how far away the user is from it. In some such examples of the present invention, the position indicator or position indicator strip 434 moves with the slider 35.

In one embodiment of the present invention, as outlined herein above, a steerable control system is provided comprising a control system within the handle (comprising an actuation mechanism) coupled to a sheath or catheter, where the control system provides a feedback mechanism 300 comprising a visual feedback mechanism 310, comprising a mechanical feedback mechanism 410 that provides an indication of the degree of curvature of the sheath or catheter and/or a neutral feedback indication as discussed herein above, may be used for steering an introducer sheath for use in an electrophysiology environment. In further alternatives, the thread pitch on the threaded portion may be increased such that the handle knob rotates less than 360 degrees in each direction and a visual or tactile indicator (as outlined further herein below) may be integrated directly into the handle to provide an indication of the sheath curvature and/or neutral zone. In alternative embodiments, the handle may be attached to and used with other steerable catheter products that may be used in other applications and may function to provide an indication of the neutral zone when deflecting the steerable products. Alternatively, the neutral feedback mechanism may be used in the handle to indicate another distal curve position.

Further details regarding an exemplary medical device with which embodiments of the present invention may be utilized are provided in U.S. provisional patent application Ser. No. 61/661,664, filed on 19 Jun. 2012, and in PCT application serial number PCT/IB2013/055013, filed in English on 18 Jun. 2013 designating the United States of America, and in PCT application serial number PCT/

IB2017/058137, filed in English on 19 Dec. 2017 designating the United States of America, all of which are incorporated herein by reference in their entirety.

Figure 3A:
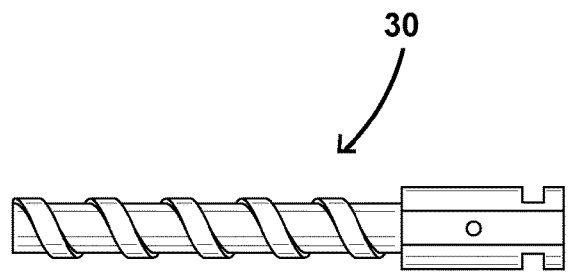
FIGS. 3A-3C are an illustration of a feedback mechanism comprising a visual feedback mechanism for steerable catheter assembly, in accordance with an embodiment of the present invention.
Figure 3B:
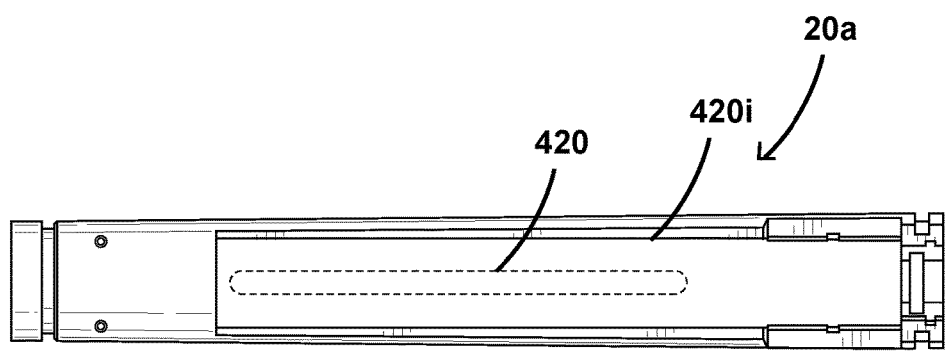
Figure 3C:
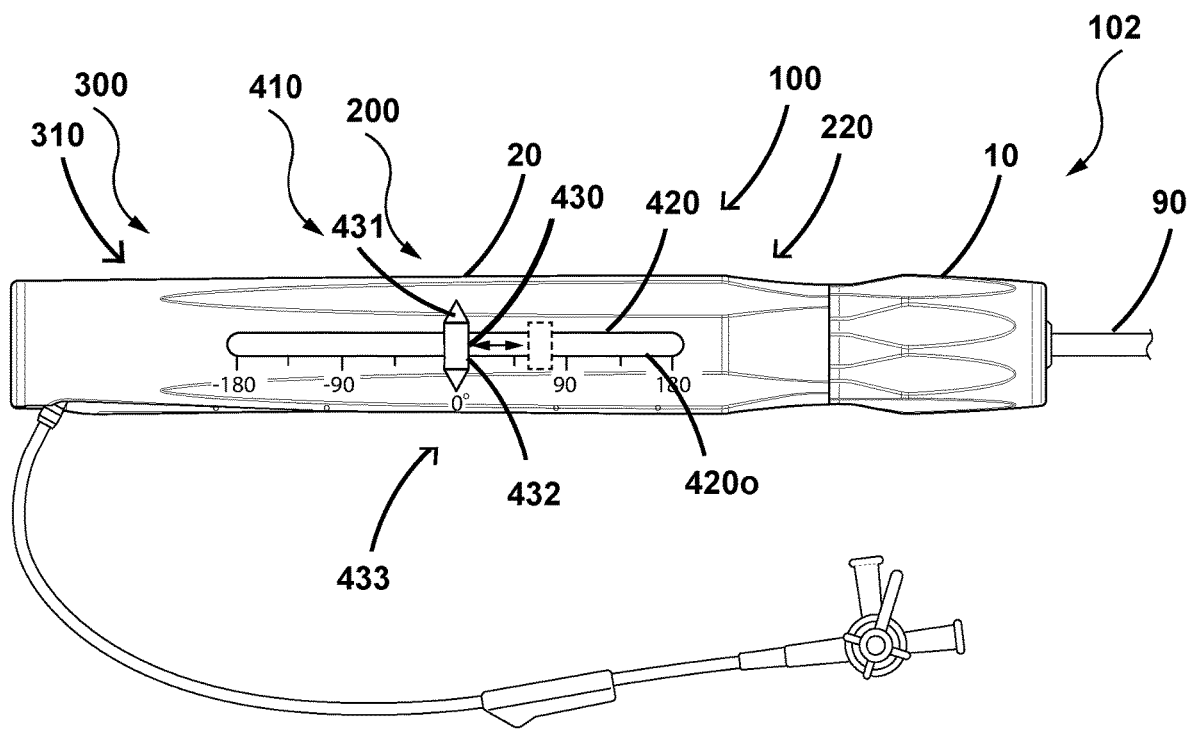
Figure 4A:
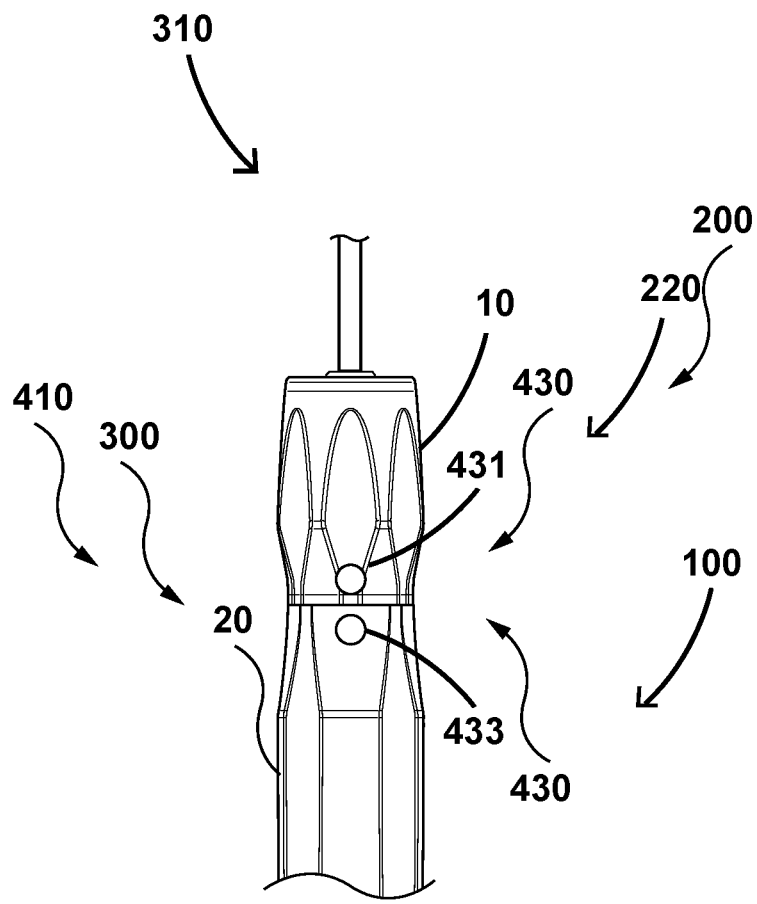
FIGS. 4A-4C are an illustration of feedback mechanisms comprising a visual feedback mechanism for a steerable catheter assembly, in accordance with an embodiment of the present invention.
Figure 4B:
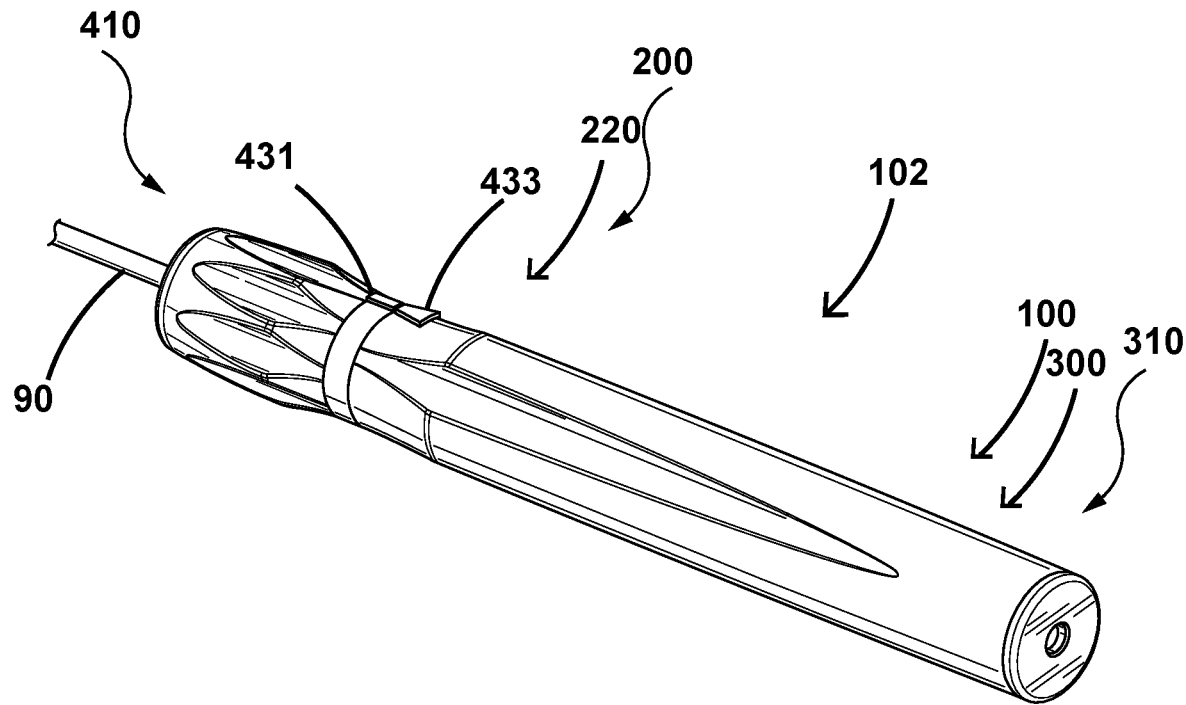

With reference now to FIGS. 4A and 4B, as well as FIGS. 3A, 3B and 3C, a feedback mechanism 300 is provided for a steerable catheter control system or assembly 102 comprising a steerable catheter control handle 100. A device comprising a sheath or catheter 90 is coupled to the steerable catheter control handle 100 and operable to be deflected upon actuation of an actuation mechanism 200. The feedback mechanism 300 comprises a visual feedback mechanism 310 comprising a mechanical feedback mechanism 410. The visual feedback mechanism 310 defines a visual indicator comprising one or more graduations or markings 430 (such as one or more alignment markings) are provided on or are associated with the actuation mechanism 200 (such as a rotation to linear actuation or translation mechanism 220, as described hereinabove).

In some such embodiments of the present invention a steerable catheter control assembly 102 is provided that comprises a bidirectional sheath 90 and a control handle 100 for operating the same. In some such examples as outlined herein the present embodiment provides a visual feedback mechanism 310 that comprises a mechanical feedback mechanism 410.

In some such examples, the mechanical feedback mechanism 410, provides an identification of curvature of the sheath or catheter 90 upon deflection and in some examples provides a neutral zone identifier that minimizes confusion for the user without misrepresenting the neutral point (i.e. where the sheath is in its substantially un-deflected state). In some such examples, the feedback mechanism 300 that is provided does not substantially impede the functionality of the device (such as the sheath or catheter 90) or the control handle 100 and as such the steerable catheter control assembly 102. In some such examples, as discussed hereinabove, in some such embodiments, even though the slide assembly 30 (and thus the slide 35) travels in both directions, an embodiment is contemplated where only one neutral or neutral position [N] is identified, which is independent of the direction that the slide assembly 30 (and thus the slide 35) is traveling in. In some such examples, the visual feedback mechanism 310 of the present invention may help reduce the risk of contradictory information or feedback. In some such embodiments of a visual feedback mechanism and additionally later (a tactile and/or audible feedback mechanism), the feedback mechanism 300 may minimize the need for the user to look at their hands or product during the procedure.

With specific reference to FIGS. 4A and 4B, in one such example, the mechanical feedback mechanism 410 comprises one or more graduations or markings 430 comprising one or more alignment markings 431 associated with the actuation mechanism 200 (such as an actuator thereof, for example a rotatable knob 10, as shown) for deflecting the catheter. The feedback mechanism 300 additionally comprises one or more graduations or markings 430 comprising one or more indicator markings 433 that are associated with or provided on a housing 20 of the control handle 100. In some such examples wherein the relative arrangement of the one or more alignment markings 431 and the one or more indicator markings 433 corresponds to and is indicative of a deflection position of the catheter and a corresponding position of the actuation mechanism 200 to provide a visual indication of the deflection position of the catheter upon actuation of the actuation mechanism 200. In some such examples, the alignment markings 431 function as a first indicator portion and the indicator markings 433 function as a second indicator portion. In one such example as shown, movement or actuation of the knob 10 causes a movement of the alignment markings 431 with respect to the indicator markings 433.

Figure 4C:
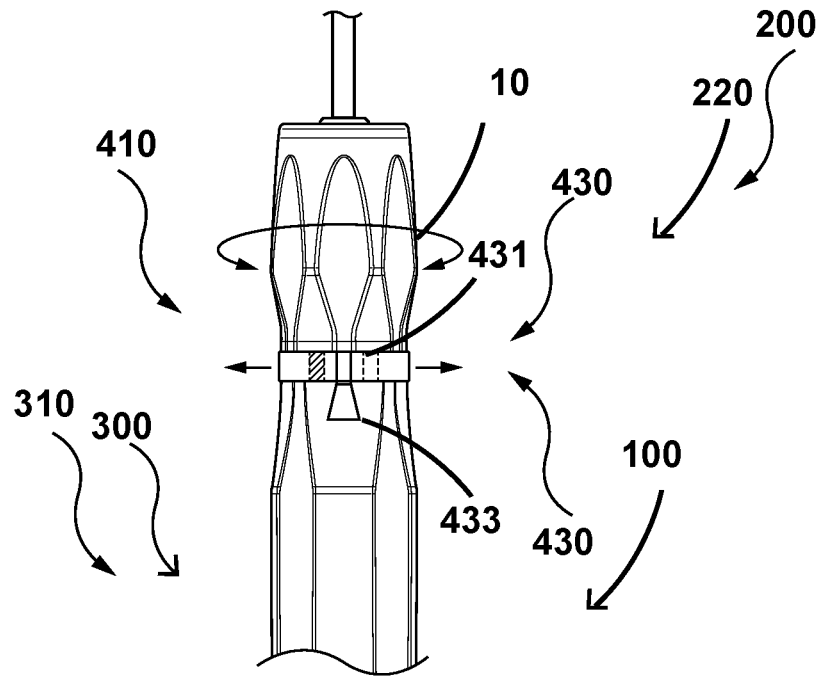
Figure 4D:
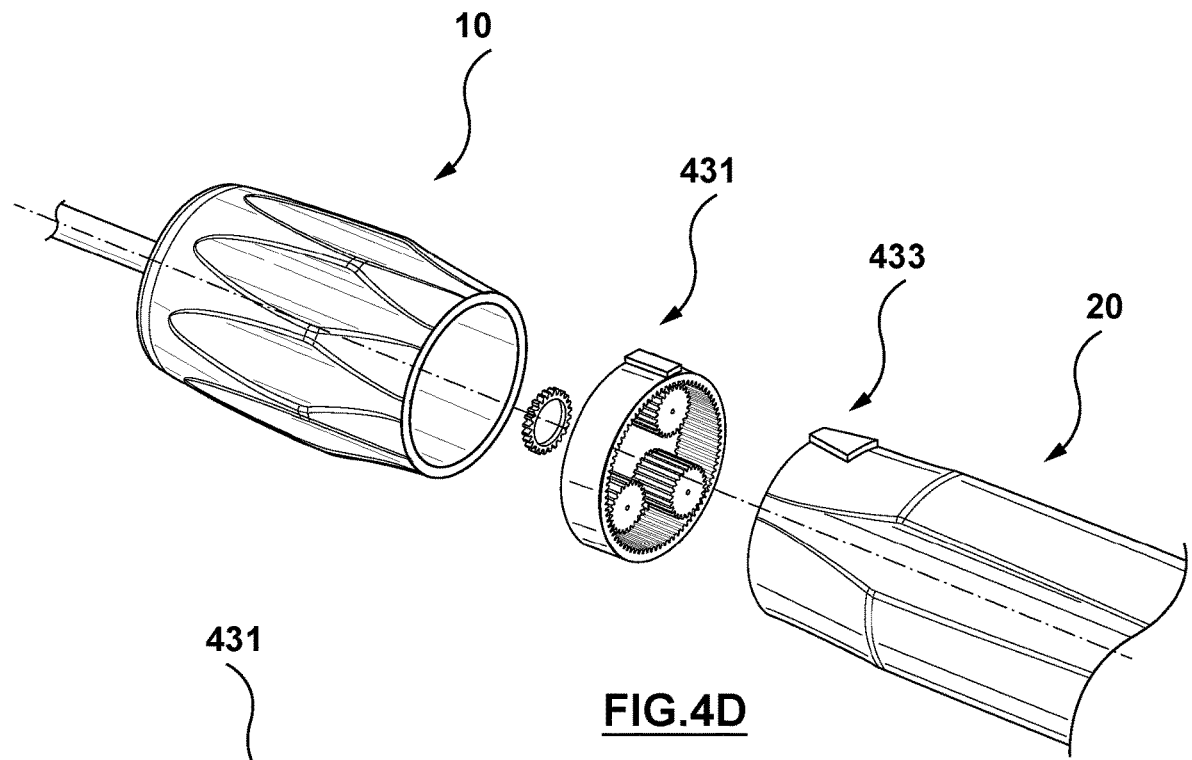
FIGS. 4D-4E are an illustration of feedback mechanisms comprising a visual feedback mechanism for a steerable catheter assembly, in accordance with an embodiment of the present invention.
Figure 4E:
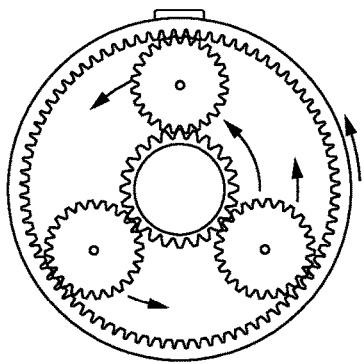

FIGS. 4D-4E are an illustration of a feedback mechanism comprising a visual feedback mechanism 310 comprising a mechanical feedback mechanism 410 for a steerable catheter assembly, in accordance with an embodiment of the present invention. In one such example, the mechanical feedback mechanism comprises reducing gears 700. In one specific example, as shown in FIGS. 4D and 4E, the reducing gears 700 comprise an arrangement of planetary gears 720 as shown. In the specific example, the planetary gears 720 comprise an inner gear 722 coupled to the knob 10 of the control handle 100. The planetary gears 720 additionally comprise an outer ring 726 that comprises gears on an inner side thereof. In one such example, the alignment markings 431 are formed on an outer surface of the outer ring 726. The outer ring 726 is free to rotate (in other words it is not fixed to the sheath control handle 100). The outer ring 726 is coupled to the inner gear 722 via intermediate gears 724. As such, as the knob 10 is rotated it causes the inner gear 722 to rotate which causes a correlating movement of the outer ring 726 via movement of the intermediate gears 724, which causes a correlated movement of the alignment markings 431 on the outer ring 726. As such, in one such example as shown, movement or actuation of the knob 10 causes a movement of the alignment markings 431 with respect to the indicator markings 433 to provide an indication of deflection of the sheath.

With specific reference to FIGS. 3A, 3B and 3C, in some such embodiments of the present invention a visual feedback mechanism 310 is provided that also comprises a mechanical feedback mechanism 410. Similar to embodiments outlined herein above with respect to FIGS. 4A-4C, the mechanical feedback mechanism 410 comprises one or more graduations or markings 430 comprising one or more alignment markings 431 associated with the actuation mechanism 200 for deflecting the catheter 90. In the specific example shown, an alignment markings 431 is provided on an additional component 432 that is coupled to or forms a part of the slide assembly 30. In the specific example, as shown in FIG. 3C, the additional component 432 forms the alignment feature or alignment marking 431. The feedback mechanism 300 additionally comprises one or more graduations or markings 430 comprising one or more indicator markings 433 that are associated with or provided on a housing 20 of the control handle 100.

In some such examples, a slot 420o is formed in the in the outer handle such as housing 20 (or in other words a slot is cut-out in the housing 20) forming the window 420. As shown in FIG. 3C, one or more graduations or markings 430 comprising one or more indicator markings 433 are provided adjacent the window 420 formed within the housing or specifically outer housing 20. In some such embodiments, where the control handle 100 additionally comprises an inner housing 20a, a slot 420i is provided in the inner handle component (such as an inner housing 20a) that corresponds to the slot 420i in the outer housing 20.

As outlined previously for FIGS. 4A-4C, the relative arrangement of the one or more alignment markings 431 and the one or more indicator markings 433 upon actuation of the actuation mechanism 200, corresponds to and is indicative of a deflection position of the catheter and a corresponding position of the actuation mechanism 200 to provide a visual indication of the deflection position of the catheter. In some such examples, the one or more alignment markings 431 function as a first indicator portion and the indicator markings 433 function as a second indicator portion.

In other words, as the knob 10 is actuated, the slide assembly 30 (and as such the slider 35) moves (for example up and down) within the outer handle housing 20 as well the inner handle or housing 20a.

In some such examples, graduations or markings 430 such as alignment markings 431 such as for example a scale (as shown in FIG. 3C) are added to the outer handle or housing 20 for indicating neutral position [N] and the bi-directional curve (for example in degrees). Additionally, in other embodiments the one or more graduations or markings 430 comprising one or more indicator markings 433 comprise a bump that is added to the outer handle or housing 20 that is operable to correlate or match up with or are visible in reference to the graduations or markings comprising the one or more alignment markings 431 associated with the slide assembly 30 to allow for identification of the degree of curvature or deflection or the distance from the neutral position. In some such examples, this information may be provided tactically.

As noted above, some such embodiments of the present invention provide a visual and/or tactile curve angle feedback. Some such embodiment of the present invention provide feedback to the user to mitigate the risk of confusion to the user such as for example related to how much the catheter has been deflected or whether it is being curved or being straightened, or additionally whether it is in its substantially un-deflected or in other words neutral zone position or how far away they are from it.

As such, some embodiments of the present invention as outlined in the present disclosure provide a method for identifying the neutral zone and curve angle through visual and/or tactile feedback.

Figure 5A:
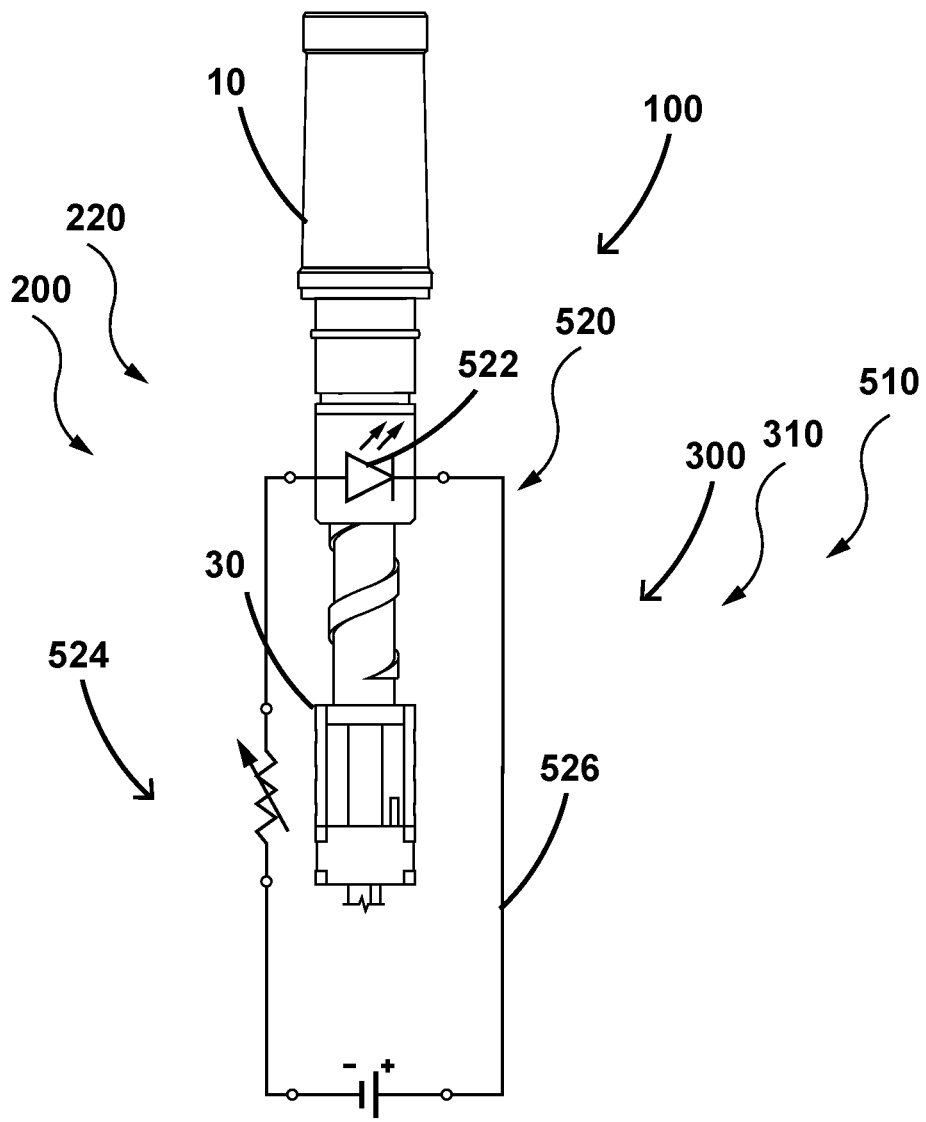
FIG. 5A is an illustration of a feedback mechanism comprising a visual feedback mechanism for a steerable catheter assembly, in accordance with an alternate embodiment of the present invention.
Figure 5B:
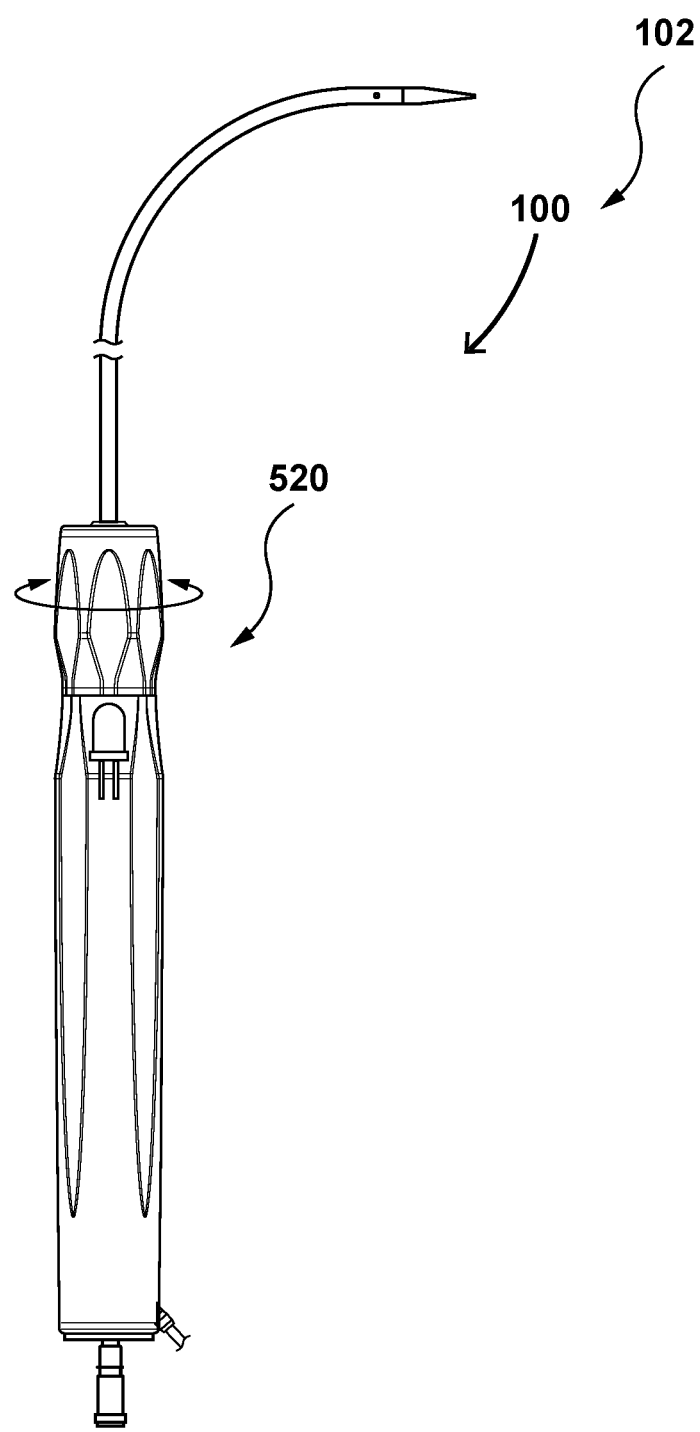
FIG. 5B is an illustration of a feedback mechanism for a steerable catheter assembly, in accordance with an alternate embodiment of the present invention.

With reference now to FIG. 5A, in accordance with an embodiment of the present invention, a feedback mechanism 300 is shown comprising a visual feedback mechanism 310 for a steerable catheter control handle system or assembly 102 (as shown in FIG. 5B), the assembly comprising an actuation mechanism 200 comprising a rotation to linear translation or actuation mechanism or system 220 (where in one such example a control handle 100 is provided comprising knob 10 (for example comprising an inner knob 10a and a slide assembly 30 translatable within a handle housing 20). In the specific example shown in FIG. 5A, the visual feedback mechanism 310 comprises an electrical feedback mechanism 510.

In one such example as shown, the electrical feedback mechanism 510 comprises a light emitting source or device 520, as shown in FIG. 5A. The light emitting source or device 520 [such as an LED 522] has an active state where the light emitting source is operable to emit light and a passive state where the light emitting source is off or in its inactive configuration. The electrical feedback mechanism 510 additionally comprises a sensor 524 that is coupled to the light emitting source or device 520 (for example via a circuit 526) for detecting a position of a portion of the actuation mechanism 200 (such as the rotation to linear actuation or translation mechanism). The light emitting source or device 520 is operable to be in its active state (where it lights up) upon detection of the position of the portion of the actuation mechanism 200 (such as the slide assembly 30—specifically the slide 35 of the slide assembly 30) by the sensor 524. In some such examples, when the light emitting source or device 520 is in its active state (for example lights up), it corresponds to and is indicative of a deflection position of the catheter and a corresponding position of the actuation mechanism 200 to provide a visual indication of the deflection position of the catheter upon actuation of the actuation mechanism 200. As noted above, in some examples the light emitting source or device 520 comprises an LED 522.

In additional embodiments of the present invention, as shown in FIGS. 6A-6C, 7A-7C and 8A-8C a feedback mechanism 300 is provided, where the feedback mechanism 300 provides sensory feedback. In some such example, the feedback mechanism provides comprises a tactile feedback mechanism 320 that provides a tactile indication. In some such examples as described herein, the tactile feedback mechanism 320 comprises a mechanical feedback mechanism 410. As above, a feedback mechanism 300 is provided for a steerable medical device such as a catheter 90 comprising a control handle 100 comprising an actuation mechanism 200 (such as a rotation to linear system 220) for deflecting a device such as a catheter 90. The device (such as the catheter 900 is coupled to the control handle 100 and operable to be deflected upon actuation of the actuation mechanism 200. The feedback mechanism 300a provides an indication of the deflection of the device (such as a catheter 90). The feedback mechanism 300 is associated with the actuation mechanism 200 for deflecting the device (such as a catheter 90).

Figure 6A:
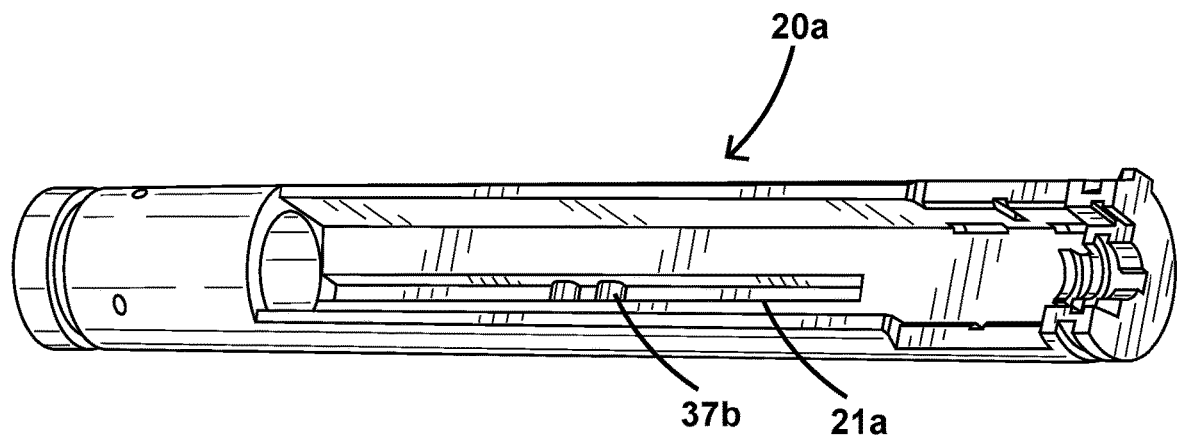
FIGS. 6A-6C are an illustration of a feedback mechanism for steerable control handle, in accordance with an alternate embodiment of the present invention.
Figure 6B:
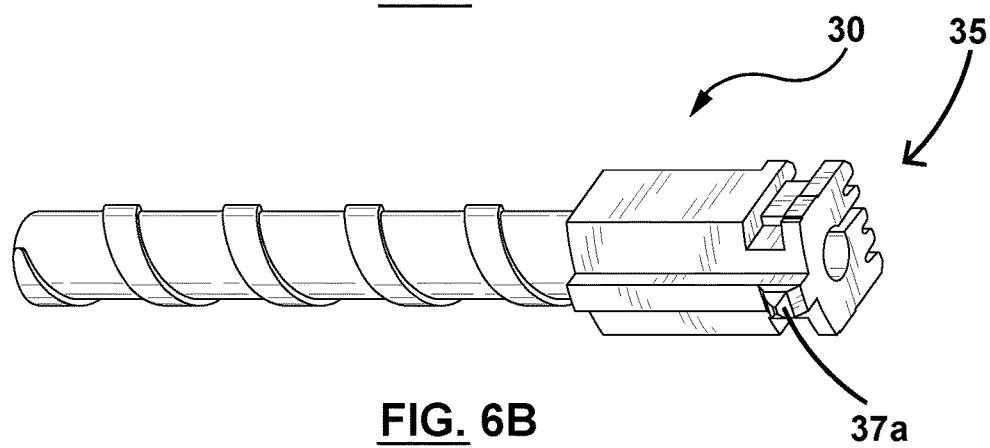
Figure 6C:
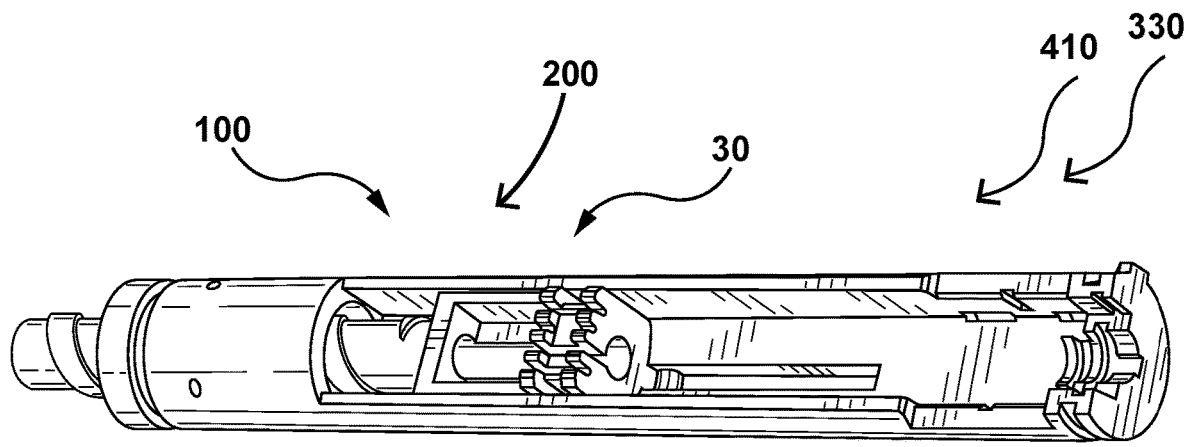

Specifically with reference to FIGS. 6A, 6B and 6C, the mechanical feedback mechanism 410 comprises a second indicator portion 37b associated with a housing or in other words a portion of the housing (such as inner housing 20a) of the control handle and a first indicator portion 37a associated with the actuation mechanism 200 for deflecting the catheter. The interaction between the first and second indicator portions (37a, 37b) corresponds to and is indicative of a deflection position of the catheter and a corresponding position of the actuation mechanism 200 (such as a position of the actuator with respect to a housing of the handle such as a position of the knob 10 with respect to a portion of the handle housing) to provide a tactile indication of the deflection position of the catheter upon actuation of the actuation mechanism 200.

More specifically, as shown in FIGS. 6A-6C, the tactile feedback 320 comprises the mechanical feedback mechanism 410 provides or adds tactile feedback for indicating sheath deflection. As before the mechanical feedback mechanism 410 comprises a first indicator portion 37a on the bottom of the slide portion 35 of the slide assembly 30 such as fin (as shown in FIG. 6B) that is operable to interact with the second indicator portion 37b such as one or more ridges or bumps on the inner housing 20a (as shown in FIG. 6A, for example along a track 21a of the inner housing 20a). The first indicator portion 37a is operable to interact with the second indicator portion 37b as the slide assembly 30 moves there against as shown in FIG. 6C, indicating the amount of deflection or the state of the sheath or catheter with respect to how much it is curved, or as shown in FIGS. 6A-6C, the position of the neutral zone where the sheath 90 is in its substantially un-deflected state.

Figure 7A:
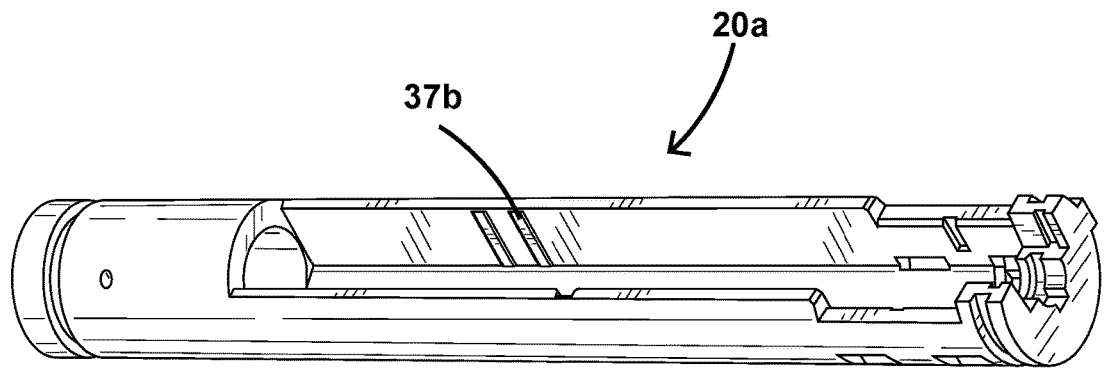
FIGS. 7A-7C are an illustration of a feedback mechanism for steerable control handle, in accordance with an alternate embodiment of the present invention.
Figure 7B:
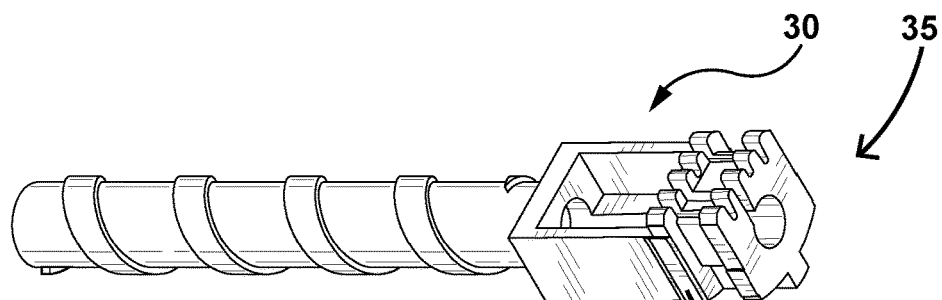
Figure 7C:
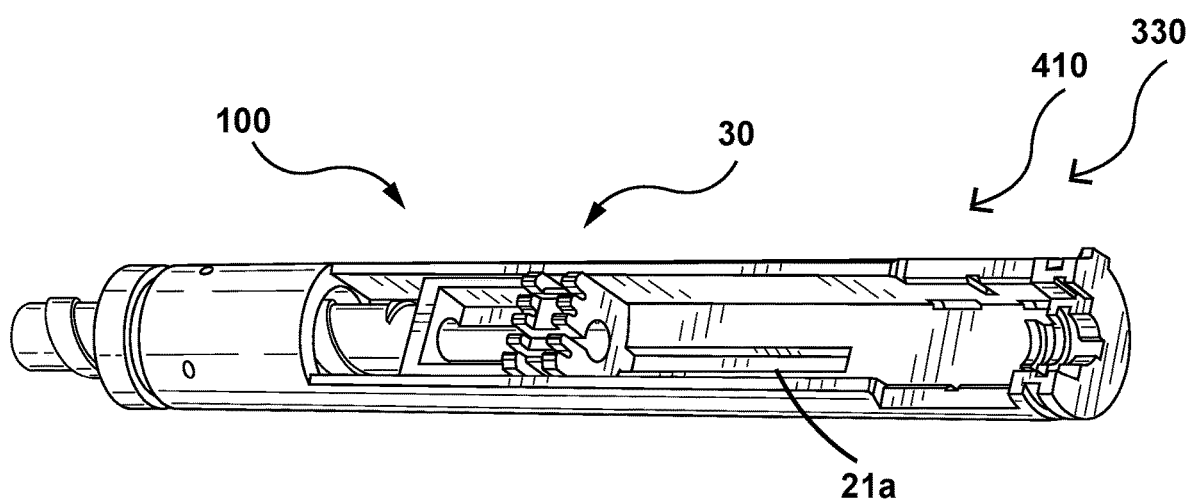

In another such embodiment of the present invention, as shown in FIGS. 7A-7C, the tactile feedback mechanism 320 comprises mechanical feedback mechanism 410 for providing or adding tactile feedback for indicating sheath deflection. As before the mechanical feedback mechanism 410 comprises a first indicator portion 37a on a side of the slide or slide portion 35 of the slide assembly 30 such as a side bump (as shown in FIG. 7B) that is operable to interact with the second indicator portion 37b such as one or more side bumps on the inner housing 20a (as shown in FIG. 7A, for example along an inner wall of the inner housing 20a). The first indicator portion 37a is operable to interact with the second indicator portion 37b as the slide assembly 30 moves there against as shown in FIG. 7C, creating resistance, indicating the amount of deflection or the state of the sheath or catheter with respect to how much it is curved, or as shown in FIGS. 7A-7C, the position of the neutral zone where the sheath 90 is in its substantially un-deflected state.

Figure 8A:
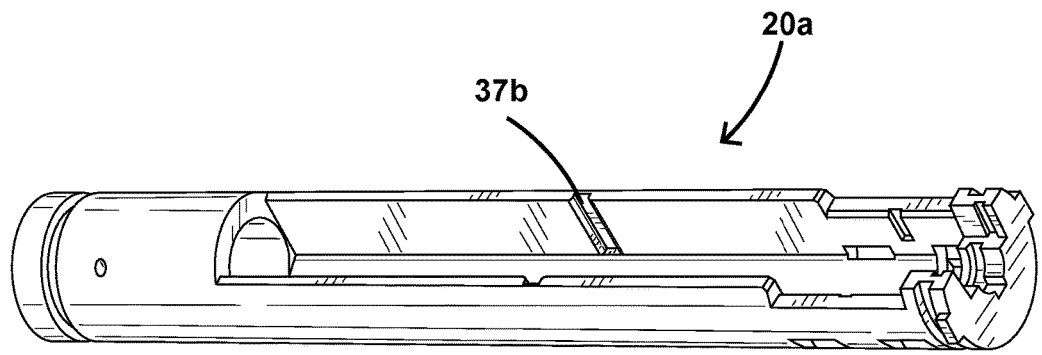
FIGS. 8A-8C are an illustration of a feedback mechanism for steerable control handle, in accordance with an alternate embodiment of the present invention.
Figure 8B:
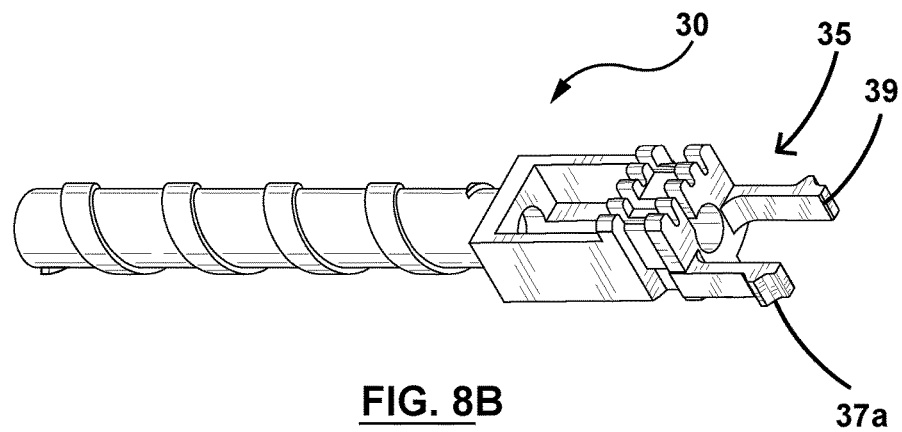
Figure 8C:
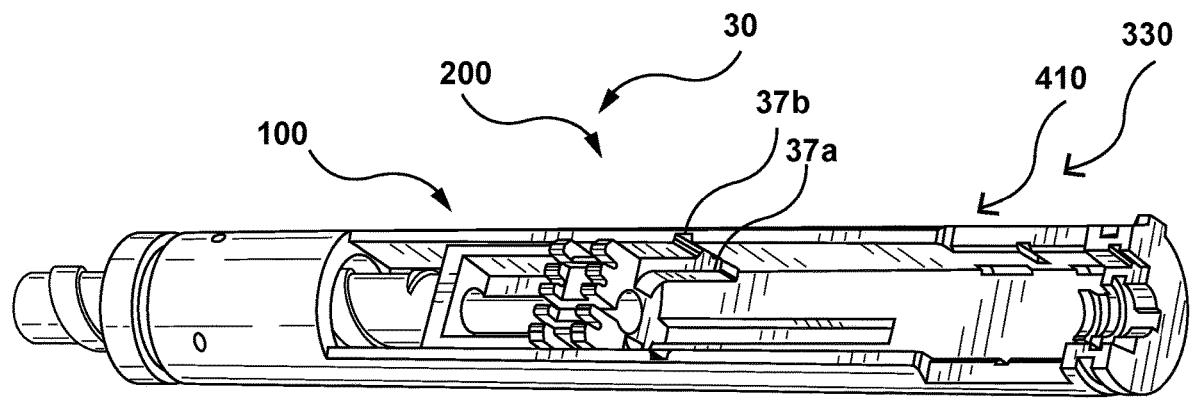

In another such embodiment of the present invention, as shown in FIGS. 8A-8C, the tactile feedback mechanism 320 comprises the mechanical feedback mechanism 410 that provides or adds tactile feedback for indicating sheath deflection. As before, the mechanical feedback mechanism 410 comprises a first indicator portion 37a on a side of the slide portion 35 of the slide assembly 30 such as a side bump along a cantilever portion 39 of the slide assembly (as shown in FIG. 8B) that is operable to interact with the second indicator portion 37b such as one or more grooves on the inner housing 20a (as shown in FIG. 8A, for example along an inner wall of the inner housing 20a), thus creating a resistive feel or a feeling of resistance. The first indicator portion 37a is operable to interact with the second indicator portion 37b as the slide assembly 30 moves there against as shown in FIG. 8C, for example by being received within the one or more grooves of the second indicator portion 37b, indicating the amount of deflection or the state of the sheath or catheter 90 with respect to how much it is curved, or as shown in FIGS. 8A-8C, the position of the neutral zone where the sheath 90 is in its substantially un-deflected state.

In additional embodiments of the present invention, with reference to FIGS. 6A-6C, 7A-7C, and 8A-8C, a feedback mechanism 300 is provided, where the feedback mechanism 300 provides sensory feedback. In some such example, the feedback mechanism 300 comprises an audible feedback mechanism 330 that provides an audible indication. The audible feedback mechanism 330 comprises a mechanical feedback mechanism 410. As above, a steerable medical device assembly or system is provided that provides feedback. The assembly or system comprises a control handle and a catheter 90 coupled thereto. In some embodiments a control handle 100 is provided that comprises an actuation mechanism 200 (such as a rotation to linear system 220) for deflecting a device such as a catheter 90. The device (such as the catheter 90) is coupled to the control handle 100 and operable to be deflected upon actuation of the actuation mechanism 200. The feedback mechanism 300 provides an indication of the deflection of the device (such as a catheter 90). The feedback mechanism 300 is associated with the actuation mechanism 200 for deflecting the device (such as a catheter 90).

In some such embodiments, with reference again to FIGS. 6A-6C, 7A-7C, and 8A-8C, the audible feedback mechanism 330 provides an audible indication. The audible feedback mechanism 330 comprises a mechanical feedback mechanism 410, where the mechanical feedback mechanism comprises a second indicator portion 37b associated with a housing (such as inner housing 20a) of the control handle, and a first indicator portion 37a associated with the actuation mechanism 200 (such as component thereof such as the slide assembly 30) for deflecting the catheter. As noted previously, the interaction between the first and second indicator portions (37a, 37b) corresponds to and is indicative of a deflection position of the catheter 90 and a corresponding position of the actuation mechanism 200 to provide an audible indication of the deflection position of the catheter upon actuation of the actuation mechanism, as the two indicator portions (37a, 37b) interact with one another for example by creating resistance between the indicator portions (37a, 37b).

Figure 9A:
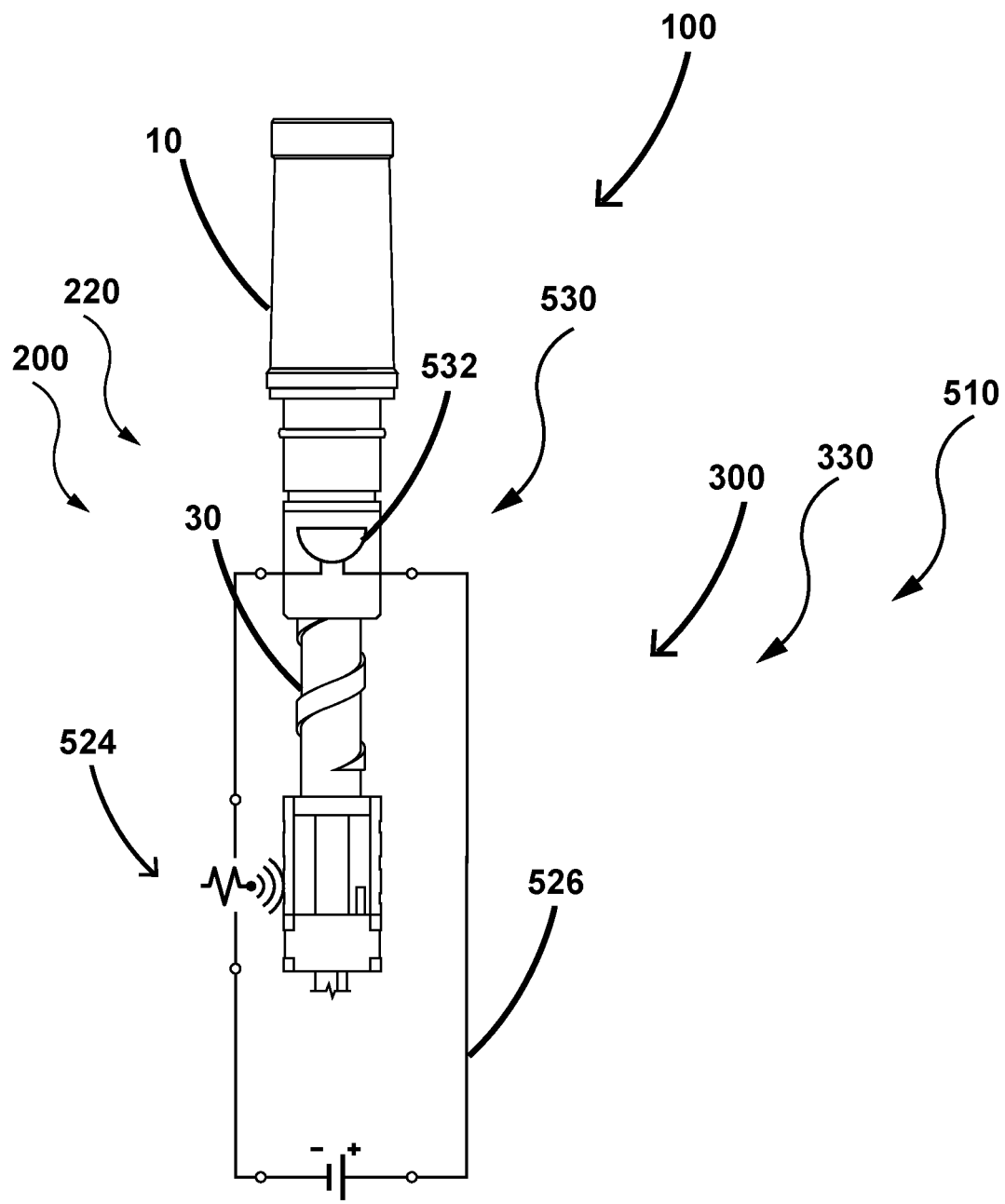
FIG. 9A is an illustration of a feedback mechanism for steerable control handle comprising an audible feedback mechanism, in accordance with an alternate embodiment of the present invention.

With reference now to FIG. 9A, in accordance with an embodiment of the present invention, a feedback mechanism 300 is shown comprising an audible feedback mechanism 330 for a steerable catheter control handle system or assembly 102 (as shown in FIG. 5B), In the specific example shown in FIG. 9A, the audible feedback mechanism 330 comprises an electrical feedback mechanism 510. In one such example as shown, the electrical feedback mechanism 510 comprises a sound emitting device 530, as shown in FIG. 9A, the sound emitting device or source 530 [such as an buzzer 532] has an active state where the sound emitting device or source 530 is operable to emit a sound and a passive state where the sound emitting device 530 is off or in its inactive configuration. The electrical feedback mechanism 510 additionally comprises a sensor 524 coupled to the sound emitting device or source 530 (for example via a circuit 526) for detecting a position (of a portion) the actuation mechanism 200 (such as the rotation to linear actuation or translation mechanism 220).

The sound emitting device or source 530 is operable to be in its active state (where it creates a sound) upon detection of the position of the actuation mechanism 200 (such as the slide assembly 30—specifically the slide 35 of the slide assembly 30) by the sensor 524. In some such examples, where the sound emitting source or device 530 is in its active state (for example creates a sound), the active state corresponds to and is indicative of a deflection position of the catheter and a corresponding position of the actuation mechanism 200 to provide an audible indication of the deflection position of the catheter upon actuation of the actuation mechanism 200. As noted above, in some examples, the sound emitting device or source 530 comprises a buzzer 532.

In some embodiments of the present invention, the feedback mechanism 300, the feedback mechanism 300 provides an indication of degree of deflection of the catheter upon actuation of the actuation mechanism 200.

In some embodiments, the feedback mechanism 300 provides an indication of a neutral zone of the control handle and the catheter. In other words, the feedback mechanism 300 provides an indication that indicates a neutral zone of the control handle and the catheter, upon the control handle and the catheter being in the neutral zone. As such, some embodiments of the present invention provide a neutral zone feedback mechanism for a steerable control handle. In some such examples, the feedback mechanism 300 provides an indication upon the actuation mechanism and the catheter exiting the neutral zone.

In some embodiments of the present invention, the actuation mechanism 200 comprises [a rotation to linear translation mechanism 220 where rotation of an actuator causes linear movement of a component of the actuation mechanism to deflect the catheter]. In some such embodiments the actuation mechanism 200 comprises an actuator comprising a control knob 10 and a slide assembly 30 that is coupled to the control knob 10 via a threadable arrangement or engagement (for example between external threads along a bolt or shaft 32 of the slide assembly 30 and corresponding inner threads of the control knob 10), the slide assembly 30 is operable to coupled to the catheter (for example via one or more control or pull wires) for example where a proximal end of the one or more control wires is coupled to the slide assembly 30, and a distal end of the one or more control wires is coupled to the catheter (for example a distal end of the catheter). In some such embodiments, the actuation of the control knob 10 via rotational movement thereof results in linear movement of the slide assembly 30 to deflect the device (such as a catheter 90).

In some embodiments of the present invention, the feedback mechanism 300 provides an indication of the deflection of the device in absence of visual feedback of the deflection of the device such as a catheter.

In some embodiments of the present invention, the feedback mechanism 300 comprises a mechanical feedback mechanism 410.

In some embodiments of the present invention, the feedback mechanism 300 comprises an electrical feedback mechanism 510.

The embodiment(s) of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A steerable medical device assembly for deflecting a catheter comprising:
    a control handle comprising an actuation mechanism;
    the actuation mechanism comprising a control knob and a slide assembly, wherein the control knob has internal threads and the slide assembly has external threads corresponding to the internal threads of the control knob whereby actuation of the control knob via rotational movement results in linear translation of the slide assembly;
    the catheter coupled to the control handle and operable to be deflected upon actuation of the actuation mechanism; and
    a mechanical feedback mechanism for providing an indication of degree of deflection of the catheter upon actuation of the actuation mechanism, wherein the mechanical feedback mechanism comprising a first indicator portion associated with the slide assembly and a second indicator portion associated with an inner housing of the control handle, wherein the first indicator portion comprises a bump on an outside of the slide assembly and the second indicator portion comprises one or more bumps on an inside surface of the inner housing;
    wherein, upon actuation of the actuation mechanism, the first indicator portion is operable to interact with the second indicator portion as the slide assembly moves along an inner wall of the inner housing that corresponds to and is indicative of a deflection position of the catheter and a corresponding position of the actuation mechanism to create a tactile feeling of resistance to provide a tactile indication of the deflection position of the catheter; and
    wherein the mechanical feedback mechanism further provides a neutral zone identifier to indicate the catheter is in an undeflected neutral position.

2. The steerable medical device assembly of claim 1, wherein the mechanical feedback mechanism comprises a visual feedback mechanism that provides a visual indication.

3. The steerable medical device assembly of claim 2, wherein the visual feedback mechanism comprises one or more alignment markings.

4. The steerable medical device assembly of claim 3, wherein the mechanical the mechanical feedback mechanism comprises:
    a window that is formed within a housing of the control handle; and
    the one or more alignment markings associated with the actuation mechanism for deflecting the device; and
    wherein a visibility of the one or more alignment markings through the window corresponds to and is indicative of the deflection position of the device and the corresponding position of the actuation mechanism to provide a visual indication of the deflection position of the device upon actuation of the actuation mechanism.

5. The steerable medical device assembly of claim 3, wherein the mechanical feedback mechanism comprises:
    the one or more alignment markings associated with the actuation mechanism for deflecting the device; and
    one or more indicator markings that are associated with a housing of the control handle; and
    wherein a relative arrangement of the one or more alignment markings and the one or more indicator markings corresponds to and is indicative of the deflection position of the device and the corresponding position of the actuation mechanism to provide a visual indication of the deflection position of the device upon actuation of the actuation mechanism.

6. The steerable medical device assembly of claim 2, wherein the visual feedback mechanism comprises an electrical feedback mechanism.

7. The steerable medical device assembly of claim 6, wherein the electrical feedback mechanism comprises a light emitting source, wherein the light emitting source has an active state where the light emitting source is operable to emit light and a passive state where the light emitting source is off; and
    a sensor coupled to the light emitting source for detecting a position of a portion of the actuation mechanism;
    wherein the light emitting source is operable to be in the active state upon detection of the position of the portion of the actuation mechanism by the sensor, and corresponds to and is indicative of the deflection position of the device and the corresponding position of the actuation mechanism to provide a visual indication of the deflection position of the device upon actuation of the actuation mechanism.

8. The steerable medical device assembly of claim 7, wherein the light emitting source comprises a light emitting diode (LED).

9. The steerable medical device assembly of claim 1, wherein the mechanical feedback mechanism further comprises an audible feedback mechanism that provides an audible indication.

10. The steerable medical device assembly of claim 9, wherein the audible feedback mechanism comprises an electrical feedback mechanism.

11. The steerable medical device assembly of claim 10, wherein the electrical feedback mechanism comprises:
a sound emitting device, the sound emitting device has an active state where the sound emitting device is operable to emit a sound and a passive state where the sound emitting device is off; and
a sensor coupled to the sound emitting device for detecting a position of a portion of the actuation mechanism;
wherein the sound emitting source is operable to be in the active state upon detection of the position of the actuation mechanism by the sensor, wherein the active state corresponds to and is indicative of the deflection position of the device and the corresponding position of the actuation mechanism to provide an audible indication of the deflection position of the device upon actuation of the actuation mechanism.

12. The steerable medical device assembly of claim 11, wherein the sound emitting device comprises a buzzer.

13. The steerable medical device assembly of claim 1, wherein an interaction between the first and second indicator portions corresponds to and is indicative of the deflection position of the catheter and the corresponding position of the actuation mechanism to provide an audible indication of the deflection position of the catheter upon actuation of the actuation mechanism.

14. The steerable medical device assembly of claim 1, wherein the mechanical feedback mechanism provides an indication upon actuation of the actuation mechanism and the catheter exiting a neutral zone.

15. The steerable medical device assembly of claim 1, wherein the bump on the outside of the slide assembly is on a side of the slide assembly and the one or more bumps on the inside surface of the inner housing are on a side of the inner housing.

16. A steerable medical device assembly for deflecting a catheter comprising:
a control handle comprising an actuation mechanism;
the actuation mechanism comprising a control knob and a slide assembly, wherein the control knob has internal threads and the slide assembly has external threads corresponding to the internal threads of the control knob whereby actuation of the control knob via rotational movement results in linear translation of the slide assembly;
the catheter coupled to the control handle and operable to be deflected upon actuation of the actuation mechanism; and
a mechanical feedback mechanism for providing an indication of degree of deflection of the catheter upon actuation of the actuation mechanism, wherein the mechanical feedback mechanism comprising a first indicator portion associated with the slide assembly and a second indicator portion associated with an inner housing of the control handle, wherein the first indicator portion comprises a bump or a fin on a bottom of the slide assembly and the second indicator portion comprises one or more bumps on a bottom of the inner housing;
wherein, upon actuation of the actuation mechanism, the first indicator portion is operable to interact with the second indicator portion as the slide assembly moves along an inner wall of the inner housing that corresponds to and is indicative of a deflection position of the catheter and a corresponding position of the actuation mechanism to create a tactile feeling of resistance to provide a tactile indication of the deflection position of the catheter; and
wherein the mechanical feedback mechanism further provides a neutral zone identifier to indicate the catheter is in an undeflected neutral position.

17. A steerable medical device assembly for deflecting a catheter comprising:
a control handle comprising an actuation mechanism;
the actuation mechanism comprising a control knob and a slide assembly, wherein the control knob has internal threads and the slide assembly has external threads corresponding to the internal threads of the control knob whereby actuation of the control knob via rotational movement results in linear translation of the slide assembly;
the catheter coupled to the control handle and operable to be deflected upon actuation of the actuation mechanism; and
a mechanical feedback mechanism for providing an indication of degree of deflection of the catheter upon actuation of the actuation mechanism, wherein the mechanical feedback mechanism comprising a first indicator portion associated with the slide assembly and a second indicator portion associated with an inner housing of the control handle, wherein the first indicator portion comprises a side bump on an outside of the slide assembly and the second indicator portion comprises one or more grooves on an inside surface of the inner housing;
wherein, upon actuation of the actuation mechanism, the first indicator portion is operable to interact with the second indicator portion as the slide assembly moves along an inner wall of the inner housing that corresponds to and is indicative of a deflection position of the catheter and a corresponding position of the actuation mechanism to create a tactile feeling of resistance to provide a tactile indication of the deflection position of the catheter; and
wherein the mechanical feedback mechanism further provides a neutral zone identifier to indicate the catheter is in an undeflected neutral position.

18. The steerable medical device assembly of claim 17, wherein the side bump is on a side of a cantilever portion of the slide assembly and the one or more grooves are on a side of the inner housing.

* * * * *